United States Patent [19]

Zimmerman et al.

[11] Patent Number: 4,683,291
[45] Date of Patent: Jul. 28, 1987

[54] PLATELET BINDING INHIBITORS

[75] Inventors: Theodore S. Zimmerman; Zaverio M. Ruggeri, both of La Jolla; Richard Houghten, Solhna Beach, all of Calif.

[73] Assignee: Scripps Clinic and Research Foundation, La Jolla, Calif.

[21] Appl. No.: 791,872

[22] Filed: Oct. 28, 1985

[51] Int. Cl.⁴ .................... A61K 37/02; C07C 103/52
[52] U.S. Cl. .................................. 530/324; 530/325; 530/326; 530/327; 530/328; 530/329; 530/330; 514/802; 514/822; 514/834; 424/101
[58] Field of Search ............. 530/324, 325, 326, 327, 530/328, 329, 330; 514/802, 822, 834; 424/101

[56] References Cited

U.S. PATENT DOCUMENTS 4,002,602 1/1977 Goldstein ........................... 530/324
4,544,500 10/1985 Bittle et al. ........................ 530/324
4,578,079 3/1986 Ruoslahti et al. ...................... 514/2

Primary Examiner—Morton Foelak
Assistant Examiner—Nathan M. Nutter
Attorney, Agent, or Firm—Morgan & Finnegan

[57] ABSTRACT

Peptides of the general formula

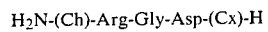

and the derivatives thereof described herein, wherein (Cx) and (Ch) each contains 1 to 20 amino acid residues and (Ch) contains at least one Lys or Arg residue, or at least one of each, inhibit platelet-fibrinogen binding and platelet-platelet aggregation and are thus useful inhibitors of cell adhesion.

33 Claims, No Drawings

PLATELET BINDING INHIBITORS

This invention relates generally to modulating cell adhesion and more specifically to inhibiting the binding of fibrinogen and other adhesive proteins (such as von Willebrand factor and fibronectin) to blood platelets, and to inhibiting the aggregation of blood platelets. Fibrinogen is a glycoprotein, present in blood plasma, which participates in platelet aggregation and in fibrin formation. Platelets are cell-like anucleated fragments, found in the blood of all mammals, which participate in blood coagulation. Interaction of fibrinogen with a receptor on the platelet membrane glycoprotein complex IIb/IIIa is known to be essential for normal platelet function.

Recent publications have described some peptides which appear to inhibit fibrinogen-platelet binding (e.g. Gly-Pro-Arg-Pro; Gly-Pro-Arg-Val-Val; Arg-Gly-Asp-Ser; Gly-Arg-Gly-Asp-Ser; and His-His-Leu-Gly-Gly-Ala-Lys-Gln-Ala-Gly-Asp-Val and its analogs missing one or both His residues). The peptides of the present invention are superior to these in ability to inhibit fibrinogen-platelet binding.

SUMMARY OF THE INVENTION

Broadly stated, the present invention comprises peptides characterized in that they inhibit fibrinogen-platelet binding and have the general formula (Ia), (Ib), (Ic) or (Id), $$H_2N\text{-}(Ch)\text{-}Arg\text{-}Gly\text{-}Asp\text{-}(Cx)\text{-}H \qquad (Ia)$$

in which (Ch) is a chain of 1 to 20 amino acid residues which contains at least one residue selected from the group consisting of Lys and Arg, and (Cx) is a chain of 1 to 20 amino acid residues. More specifically, the present invention also includes peptides of the following general formula (II):

$$H_2N\text{-}(His)_{0\text{-}2}\text{-}(D\text{-}Ala)_{0\text{-}1}\text{-}(Gly)_{0\text{-}2}\text{-}(X)_n\text{-}(Gln)_{0\text{-}1}\text{-}Arg\text{-}Gly\text{-}Asp\text{-}(Z)\text{-}H \qquad (II)$$

in which the subscript n denotes an integer from 1 to 20, each of the n amino acid residues X is independently Lys or Arg, the symbol Z represents a valine or serine residue, and His optionally carries a 2,4-dinitrophenyl group or other side-chain derivative on the imidazole nitrogen.

Such peptides are very potent inhibitors of fibrinogen-platelet binding, and also inhibit aggregation of platelets.

Also included within the scope of this invention are polymeric forms comprising repeating units of the peptide of formula (I), e.g. having the formula

wherein the degree of polymerization i can range up to 1000, or 10,000, or higher, provided that the resulting peptide is soluble in an aqueous isotonic solution 0.15 M in sodium chloride.

The invention further comprises branched peptides having any of the following formulas:

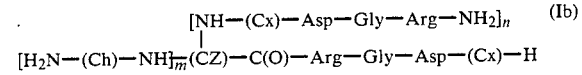

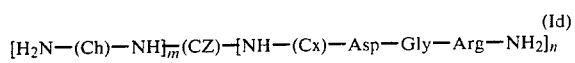

in which (Ch) and (Cx) are as defined above, each of m and n is an integer and is 1 to 10 and preferably 1 to 3, wherein the sum of (m+n) is 3 to 20 and preferably 3 to 6, and (CZ) is a straight or branched alkyl group having at least (m+n) carbon atoms and up to 20 carbon atoms.

Examples of such branched peptides include these:

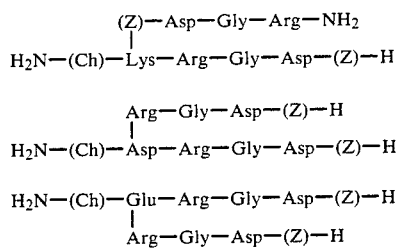

in which each Z represents serine or valine.

In addition, 1 to 20 amino acid residues can be present on the C-terminal side of the peptides described above, without detrimental effect on the $IC_{50}$. Examples of such peptides are:

H$_2$N-Lys-Ser-Arg-Lys-Arg-Gly-Asp-Ser-Ala-Asp-Arg-Asn-Tyr-H.

H$_2$N-Arg-Arg-Arg-Arg-Gly-Asp-Val-Ala-Asp-Arg-Asn-Tyr-H.

DETAILED DESCRIPTION OF THE INVENTION

The peptides of the present invention have utility in the study of fibrinogen-platelet, platelet-platelet, and cell-cell interactions. In view of their ability to inhibit fibrinogen-platelet binding and platelet aggregation, they have utility wherever it is desirable to retard or prevent the formation of a thrombus or clot in the blood (i.e. anti-thrombotic activity). In addition, in view of the findings reported herein that the peptides of the present invention act at the platelet receptors, the peptides are useful in inhibiting cell-to-cell aggregation in general.

In the formula H$_2$N-(Ch)-Arg-Gly-Asp-(Z)-H, the chain Ch preferably contains a total of four or more Lys residues, four or more Arg residues, or a total of four or more Lys and Arg residues, preferably including at least one -Lys-Lys-, -Lys-Arg-, Arg-Lys-, or -Arg-Arg- linkage. Besides the indicated Lys and/or Arg residue(s) in the chain (Ch) the chains (Ch) and (Cz) can otherwise contain any other amino acid, e.g. Ala, Cys, Asp, Glu, Phe, Gly, His, Ile, Leu, Met, Asn, Pro, Gln, Ser, Thr, Val, Trp, or Tyr. Peptides within the scope of the present invention include those having the general formula

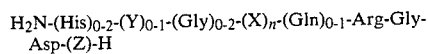

in which n is 1 to 20, each X is independently Lys or Arg, Y is Leu or Ala, and Z is Ser or Val. Of these, the preferred peptides are those in which all the residues X are all Arg, all Lys, or are alternately Lys and Arg. Of these, even more preferred are the peptides H$_2$N-(His)$_{0\text{-}2}$-(X)$_n$-Arg-Gly-Asp-Val-H, such as the following:

H₂N-Arg-Arg-Arg-Arg-Arg-Arg-Arg-Arg-Arg-Gly-Asp-Val-H
H₂N-His-His-Arg-Arg-Arg-Arg-Arg-Arg-Gly-Asp-Val-H
H₂N-His-His-Lys-Arg-Lys-Arg-Lys-Arg-Arg-Gly-Asp-Val-H
H₂N-Lys-Arg-Lys-Arg-Lys-Arg-Lys-Arg-Arg-Gly-Asp-Val-H

In the peptide structures described herein, each amino acid residue can be in the (L) or the (D) configuration unless specified otherwise.

The peptides are preferably prepared using solid phase synthesis, such as that described by Merrifield, J. Am. Chem. Soc. 85, 2149 (1964), although other equivalent chemical syntheses known in the art can also be used, such as the syntheses of Houghten, Proc. Natl. Acad. Sci. 82: 5132 (1985). Solid-phase synthesis is commenced from the C-terminus of the peptide by coupling a protected amino acid to a suitable resin, as generally set forth in U.S Pat. No. 4,244,946, issued Jan. 21, 1982 to Rivier et al., the disclosure of which is incorporated herein by reference. Examples of syntheses of this general type are set forth in U.S. Pat. Nos. 4,305,872 and 4,316,891. Discussion of the solid-phase synthesis of a 41-residue polypeptide is set forth in Science, 213, 1394–1397 (September 1981) in an article by Vale et al., which refers to a more detailed discussion of the synthesis, which appears in an article by Marke et al. in J. Am. Chem. Soc., 103, 3178 (1981).

In synthesizing the polypeptide, valine or serine having its alpha-amino group suitably protected (and, with serine, having its hydroxymethyl side chain protected) is coupled to a chloromethylated polystyrene resin or the like. After removal of the alpha-amino protecting group, as by using trifluoroacetic acid in methylene chloride, the next step in the synthesis is ready to proceed. Other standard cleaving reagents and conditions for the removal of specific amino protecting groups may be used, as described in the open literature.

The remaining alpha-amino- and side-chain-protected amino acids are then coupled stepwise in the desired order to obtain an intermediate compound connected to the resin. As an alternative to adding each amino acid separately in the synthesis, some of them may be coupled to one another prior to the addition to the growing solid-phase chain. The selection of the appropriate coupling reagents is within the skill of the art.

Common to chemical syntheses of peptides is the protection of the labile side-chain groups of the various amino acid moieties with suitable protecting groups at that site until the group is ultimately removed after the chain has been completely assembled. Also common is the protection of the alpha-amino group on an amino acid or a fragment while that entity reacts at the carboxyl group, followed by the selective removal of the alpha-amino-protecting group to allow subsequent reaction to take place at that location. Accordingly, it is common that, as a step in the synthesis, an intermediate compound is produced which includes each of the amino acid residues located in the desired sequence in the peptide chain with various of these residues having side-chain protecting groups. These protecting groups are then commonly removed substantially at the same time so as to produce the desired resultant product following purification.

Peptides composed of repeating units of the peptide of formula (I) or (II) above are made by the same procedure.

After the desired amino acid sequence has been completed, the intermediate peptide is removed from the resin support by treatment with a reagent, such as liquid HF, which not only cleaves the peptide from the resin, but also cleaves all the remaining side-chain-protecting groups. The polypeptide can then be purified by gel permeation followed by semipreparative HPLC, as described in Rivier et al., Peptides: Structure and Biological Function (1979) pp. 125–128. A purity of at least 93% or higher (based upon all peptides present) is reasonably obtainable and is preferred for clinical testing and/or use. Purity of 98% is practical; however, for certain in vitro applications, lower purity may be acceptable. Accordingly, the polypeptide is considered useful when it is in substantially pure form which, for purposes of this application, means at least about 50 weight percent, based upon all peptides present.

The peptides of the present invention can be formulated into pharmaceutical preparations for therapeutic, diagnostic, or other uses. To prepare them for intravenous administration, the compositions are dissolved in water containing physiologically compatible substances such as sodium chloride (e.g. 0.1–2.0 M), glycine, and the like and having a buffered pH compatible with physiological conditions. The amount to administer will depend on the activity of the particular compound administered, which can readily be determined by those of ordinary skill in the art. A technique for determining the effective amount to administer is described herein.

The peptide H₂N-Lys-Arg-Lys-Arg-Lys-Arg-Lys-Arg-Arg-Gly-Asp-Val-H IC$_{50}$=0.4 μM) was used in several experiments designed to clarify the mechanisms of its inhibitory activity. The peptide had similar effects when the total calcium concentration in the medium varied between 1 and 5 mM, suggesting that it did not act by decreasing the availability of the divalent cations necessary for fibrinogen binding to the GPIIb/IIIa complex of the platelet membrane. At the concentrations necessary to block fibrinogen binding to platelets, the peptide did not induce the release of $^{14}$C-serotonin from platelets, nor did it inhibit the release induced by thrombin. These experiments indicate that the peptide has no effect on the processes leading to the exposure of the fibrinogen receptor.

In addition, the affinity of fibrinogen binding to platelets was found to decrease in the presence of the peptide whereas the total number of available binding sites remained unchanged. These results demonstrated that the peptide competes with the native fibrinogen molecule for binding to the same platelet receptor, the GPIIb/IIIa complex. Accordingly, the inhibitory effect of the peptide could be overcome by increasing the fibrinogen concentration. This is at variance with the results obtained using the peptide Gly-Pro-Arg-Pro, whose inhibitory effect has been shown to increase with increasing fibrinogen concentrations. In fact, Gly-Pro-Arg-Pro is thought to interfere with fibrinogen binding to platelets by interacting with fibrinogen itself and not the platelet receptor.

The effect of the peptide on platelet aggregation was also evaluated. Complete inhibition of aggregation induced by ADP in normal platelet-rich plasma was achieved at peptide concentrations of 20 micromolar.

The following Table lists specific peptides within the scope of the present invention and their activities. IC$_{50}$ is the number of micromoles of peptide, per liter, necessary to inhibit 50% of the binding of fibrinogen present at a concentration of 60 milligrams/liter (0.176 micromoles/liter). Peptides were stored in the lyophilized state and dissolved in distilled water immediately before use. One-tenth volume of 10x modified Tyrode buffer was added before mixing with the platelet suspension. Platelets were isolated from normal platelet-rich plasma and washed by the albumin density gradient technique. Fibrinogen was purified following precipitation with glycine or polyethylene glycol 1000, and radiolabeled with $^{125}$I using Iodogen (Pierce). The results obtained using fibrinogen prepared by the two different techniques were in close agreement. In each experimental mixture, platelets in modified Tyrode buffer were stimulated with human alpha-thrombin at 22°–25° C. for 10 minutes (3.125×10$^{11}$ platelets/L and 0.25 NIHU/ml of thrombin). Hirudin (Sigma) was then added at a 25-fold excess (V/V) for 5 minutes before the addition of $^{125}$I-fibrinogen and the peptide was then tested. After these additions, the final platelet count in the mixture was 1×10$^{11}$/L, and fibrinogen was 0.176 micromolar. Separation of bound from free ligand was achieved by centrifuging 50 microliters of the mixture through 200 microliters of 20% sucrose at 12,000 g for 4 minutes. The platelet pellet was separated from the rest of the mixture, and the platelet-bound radioactivity was then determined. Non-specific binding was measured in mixtures containing a 75-fold excess of unlabeled fibrinogen. It never exceeded 5% of total binding and was subtracted from all results to obtain specific binding. Each peptide was tested at six different concentrations, and the IC$_{50}$ was derived from a plot of residual fibrinogen binding versus log of peptide concentration. All inhibitory peptides tested showed parallel dose-response curves and, when present in sufficient concentration, inhibit fibrinogen binding completely.

TABLE

| Peptide (All peptides are depicted with the amino-terminal residue on the left. All amino acids are in the L-configuration unless stated otherwise). | Typical IC$_{50}$ (micromolar) IC$_{50}$ |
|---|---|
| Arg—Arg—Arg—Arg—Arg—Arg—Arg—Arg—Arg—Gly—Asp—Val | 0.2 |
| Lys—Arg—Lys—Arg—Lys—Arg—Lys—Arg—Arg—Gly—Asp—Val | 0.4 |
| His—His—Arg—Arg—Arg—Arg—Arg—Arg—Arg—Gly—Asp—Val | 1.3 |
| His—His—Lys—Lys—Lys—Lys—Lys—Lys—Arg—Gly—Asp—Val | 1.6 |
| His—His—D-Ala—Arg—Lys—Arg—Lys—Gln—Arg—Gly—Asp—Val | 2.2 |
| His—His—D-Ala—Gly—Gly—Arg—Lys—Gln—Arg—Gly—Asp—Val | 2.8 |
| His—His—Lys—Arg—Lys—Arg—Lys—Arg—Arg—Gly—Asp—Ser | 3.1 |
| His—His—Lys—Arg—Lys—Arg—Lys—Gln—Arg—Gly—Asp—Val | 3.3 |
| Lys—Lys—Lys—Lys—Lys—Lys—Lys—Lys—Arg—Gly—Asp—Val | 4.1 |
| His—His—Leu—Arg—Lys—Arg—Lys—Gln—Arg—Gly—Asp—Val | 4.4 |
| His—His—Leu—Gly—Arg—Arg—Lys—Gln—Arg—Gly—Asp—Val | 5.4 |
| His—His—Lys—Arg—Lys—Arg—Lys—Gln—Arg—Gly—Asp—Ser | 6.2 |
| His—His—Leu—Arg—Gly—Arg—Lys—Gln—Arg—Gly—Asp—Val | 6.2 |
| His—His—Leu—Gly—Gly—Arg—Lys—Gln—Arg—Gly—Asp—Val | 6.3 |
| His—His—Leu—Arg—Gly—Lys—Lys—Gln—Arg—Gly—Asp—Val | 11.2 |
| His—His—Leu—Gly—Gly—Lys—Lys—Gln—Arg—Gly—Asp—Val | 13.2 |
| His—His—Leu—Gly—Gly—Ala—Lys—Gln—Arg—Gly—Asp—Val | 14.5 |

The published dodecapeptide His-His-Leu-Gly-Gly-Ala-Lys-Gln-Ala-Gly-Asp-Val had an IC$_{50}$ of between 48 and 83 micromolar. The published tetrapeptide Arg-Gly-Asp-Ser had an IC$_{50}$ of 48 micromolar. The previously published report that the sequence of Arg-Gly-Asp-Ser supports the function of fibronectin in promoting both the binding of fibronectin to thrombin-stimulated platelets and cell attachment confirms the present invention's utility in inhibiting cell-cell attachment and cell growth phenomena such as cancer.

What is claimed is:

1. A peptide having one of the formulas

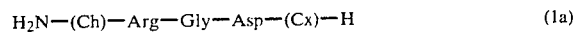 (1a)

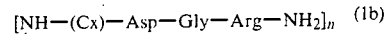 (1b)
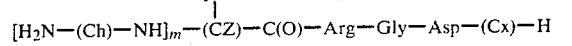

 (1c)

 (1d)

wherein:
(Ch) is a chain of 1 to 20 amino acid residues which contains at least 1 residue selected from the group consisting of Lys and Arg;
m and n are each 1-10, and (m+n) is 3-20;
(CZ) is a straight or branched alkyl group contained at least (m+n) carbon atoms and up to 20 carbon atoms;
(Cx) is a chain of 1 to 20 amino acid residues or a chemical bond with the proviso that (Cx) in formula (1a) does not include the amino acid residues, Cys, Thr or Ser; and each amino acid residue is in the (L) or (D) configuration.

2. A peptide according to claim 1 wherein Ch contains at least one -Lys-Lys-, -Lys-Arg-, -Arg-Lys-, or -Arg-Arg-moiety.

3. A peptide of the formula

H$_2$N—(His)$_{0-1}$—(Gly)$_{0-1}$—(X)$_n$—

(Gln)$_{0-1}$—Arg—Gly—Asp—Val—H wherein:
n is a integer from 1 to 20;
X in each occurrence is independently Lys or Arg;
Y is Leu or Ala;
and each amino acid residue is in the (L) or (D) configuration.

4. A peptide according to claim 3 having the formula

H₂N-(X)$_n$-Arg-Gly-Asp-Val-H
wherein:
n is an integer from 1 to 20;
each of the amino acid residues X is independently Lys or Arg; and
each amino acid residue in the peptide is in the (L) or (D) configuration.

5. A peptide according to claim 4 having the formula H₂N-(Arg)$_{n+1}$-Gly-Asp-Val-H.

6. A peptide according to claim 5 wherein n is 8.

7. A peptide according to claim 6 wherein each amino acid residue is in the (L) configuration.

8. A peptide according to claim 6 wherein each amino acid residue is in the (D) configuration.

9. A peptide according to claim 4 having the formula H₂N-(X)$_n$-Arg-Gly-Asp-Val-H wherein (X)$_n$ is -(Lys-Arg)$_i$- or -(Arg-Lys)$_i$- and i is an integer from 1 to 6.

10. A peptide according to claim 9 having the formula H₂N-Lys-Arg-Lys-Arg-Lys-Arg-Lys-Arg-Arg-Gly-Asp-Val-H.

11. A peptide according to claim 10 wherein each amino acid residue is in the (L) configuration.

12. A peptide according to claim 10 wherein each amino acid residue is in the (D) configuration.

13. A peptide according to claim 3 which has the formula H₂N-His-His-Arg-Arg-Arg-Arg-Arg-Arg-Arg-Gly-Asp-Val-H.

14. A peptide according to claim 3 which has the formula H₂N-His-His-Lys-Lys-Lys-Lys-Lys-Lys-Arg-Gly-Asp-Val-H.

15. A peptide according to claim 3 which has the formula H₂N-His-His-D-Ala-Arg-Lys-Arg-Lys-Gln-Arg-Gly-Asp-Val-H.

16. A peptide according to claim 3 which has the formula H₂N-His-His-D-Ala-Gly-Gly-Arg-Lys-Gln-Arg-Gly-Asp-Val-H.

17. A peptide according to claim 3 which has the formula H₂N-His-His-Lys-Arg-Lys-Arg-Lys-Arg-Arg-Gly-Asp-Ser-H.

18. A peptide according to claim 3 which has the formula H₂N-His-His-Lys-Arg-Lys-Arg-Lys-Gln-Arg-Gly-Asp-Val-H.

19. A peptide according to claim 3 which has the formula H₂N-Lys-Lys-Lys-Lys-Lys-Lys-Lys-Lys-Arg-Gly-Asp-Val-H.

20. A peptide according to claim 3 which has the formula H₂N-His-His-Leu-Arg-Lys-Arg-Lys-Gln-Arg-Gly-Asp-Val-H.

21. A peptide having the formula

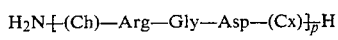

wherein (Cx) is a chain of 1 to 20 amino acid residues with the proviso that (Cx) does not include the amino acid residues, Cys, Thr, or Ser when p is 1,
(Ch) is a chain of 1 to 20 amino acid residues which contains at least 1 residue selected from the group consisting of Lys and Arg; each amino acid residue is in the (L) or (D) configuration; and p is a value such that the peptide is soluble in an aqueous isotonic solution 0.15 M in sodium chloride.

22. A method for inhibiting the binding of fibrinogen to platelets comprising contacting the platelets with a peptide according to claim 1 in an amount of said peptide effective to inhibit said binding.

23. A method for inhibiting the binding of fibrinogen to platelets comprising contacting the platelets with a peptide according to claim 4 in an amount of said peptide effective to inhibit said binding.

24. A method for inhibiting the binding of fibrinogen to platelets comprising contacting the platelets with a peptide according to claim 6 in an amount of said peptide effective to inhibit said binding.

25. A method for inhibiting the binding of fibrinogen to platelets comprising contacting the platelets with a peptide according to claim 10 in an amount of said peptide effective to inhibit said binding.

26. A method for inhibiting aggregation of cells to each other comprising contacting the cells with a peptide according to claim 1 in an amount of said peptide effective to inhibit said aggregation.

27. A method for inhibiting aggregation of platelets to each other comprising contacting the platelets with a peptide according to claim 1 in an amount of said peptide effective to inhibit said aggregation.

28. A method for inhibiting aggregation of cells to each other comprising contacting the cells with a peptide according to claim 4 in an amount of said peptide effective to inhibit said aggregation.

29. A method for inhibiting aggregation of platelets to each other comprising contacting the platelets with a peptide according to claim 4 in an amount of said peptide effective to inhibit said aggregation.

30. A method for inhibiting aggregation of cells to each other comprising contacting the cells with a peptide according to claim 6 in an amount of said peptide effective to inhibit said aggregation.

31. A method for inhibiting aggregation of platelets to each other comprising contacting the platelets with a peptide according to claim 6 in an amount of said peptide effective to inhibit said aggregation.

32. A method for inhibiting aggregation of cells to each other comprising contacting the cells with a peptide according to claim 10 in an amount of said peptide effective to inhibit said aggregation.

33. A method for inhibiting aggregation of platelets to each other comprising contacting the platelets with a peptide according to claim 10 in an amount of said peptide effective to inhibit said aggregation.

* * * * *

UNITED STATES PATENT AND TRADEMARK OFFICE
CERTIFICATE OF CORRECTION

PATENT NO. : B1 4,683,291

DATED : July 3, 1990

INVENTOR(S) : Theodore S. Zimmerman et al.

It is certified that error appears in the above-identified patent and that said Letters Patent is hereby corrected as shown below:

Column 3:

In claim 57, line 3, cancel "(Lys)" and insert --(Arg-Lys)--.

Signed and Sealed this

Twenty-eighth Day of June, 1994

Attest:

BRUCE LEHMAN

*Attesting Officer*         *Commissioner of Patents and Trademarks*

UNITED STATES PATENT AND TRADEMARK OFFICE
CERTIFICATE OF CORRECTION

PATENT NO. : B1 4,683,291
DATED : July 3, 1990
INVENTOR(S) : Zimmerman et al

It is certified that error appears in the above-indentified patent and that said Letters Patent is hereby corrected as shown below:

Column 1, after the title insert --This invention was made with government support under Grant Number HL 15491 awarded by The National Institute of Health. The government has certain rights to this invention.--

Signed and Sealed this

Tenth Day of January, 199

*Attest:*

BRUCE LEHMAN

*Attesting Officer*   *Commissioner of Patents and Trademarks*

REEXAMINATION CERTIFICATE (1321st)
United States Patent [19]
Zimmerman et al.

[11] B1 4,683,291
[45] Certificate Issued    Jul. 3, 1990

[54] PLATELET BINDING INHIBITORS

[75] Inventors: Theodore S. Zimmerman; Zaverio M. Ruggeri, both of La Jolla; Richard Houghten, Solhna Beach, all of Calif.

[73] Assignee: Scripps Clinic and Research Foundation, La Jolla, Calif.

Reexamination Reqs:st:
No. 90/001,537, Jun. 20, 1988
No. 90/001,564, Jul. 21, 1988

Reexamination Certificate for:
Patent No.: 4,683,291
Issued: Jul. 28, 1987
Appl. No.: 791,872
Filed: Oct. 28, 1985

[51] Int. Cl.$^5$ .................. A61K 37/02; C07C 215/06; C07C 215/24
[52] U.S. Cl. .................................... 530/324; 530/325; 530/326; 530/327; 530/328; 530/329; 530/330; 424/101; 514/802; 514/822; 514/834
[58] Field of Search ............... 530/324, 325, 326, 327, 530/328, 329, 330; 514/802, 822, 834; 424/101

[56] References Cited
U.S. PATENT DOCUMENTS
4,578,079 3/1986 Ruoslahti et al. ................. 623/11
4,614,517 9/1986 Ruoslahti et al. ................. 623/11

OTHER PUBLICATIONS
Pierschbacher et al., "Variants of the Cell Recognition Site of Fibronectin That Retain Attachment-Promoting Activity", Proc. Natl. Acad. Sci. U.S.A. 81, 5985-5988, Oct. 1984.

Primary Examiner—Nathan M. Nutter

[57] ABSTRACT

Peptides of the general formula

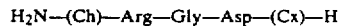

$$H_2N-(Ch)-Arg-Gly-Asp-(Cx)-H$$

and the derivatives thereof described herein, wherein (Cx) and (Ch) each contains 1 to 20 amino acid residues and (Ch) contains at least one Lys or Arg residue, or at least one of each, inhibit platelet-fibrinogen binding and platelet-platelet aggregation and are thus useful inhibitors of cell adhesion.

REEXAMINATION CERTIFICATE ISSUED UNDER 35 U.S.C. 307

THE PATENT IS HEREBY AMENDED AS INDICATED BELOW.

AS A RESULT OF REEXAMINATION, IT HAS BEEN DETERMINED THAT:

Claims 1-33 are cancelled.

New claims 34-72 are added and determined to be patentable.

34. A peptide having one of the formulas

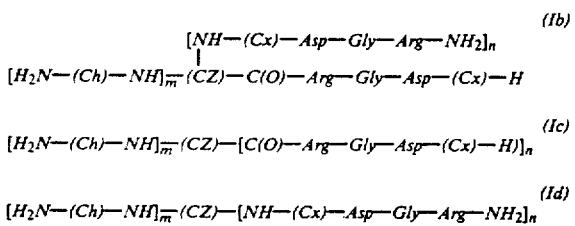

wherein:
(Ch) is a chain of 1 to 20 amino acid residues which contains at least 1 residue selected from the group consisting of Lys and Arg;
m and n are each 1-10, and (m+n) is 3-20;
(CZ) is a straight or branched alkyl group containing at least (m+n) carbon atoms and up to 20 carbon atoms;
(Cx) is a chain of 1 to 20 amino acid residues; and each amino acid residue is in the (L) or (D) configuration.

35. A peptide according to claim 34 where (Ch) contains at least one -Lys-Lys-, -Lys-Arg-, -Arg-Lys- or -Arg-Arg- linkage.

36. A peptide having the formula H₂N-(Ch)-Arg-Gly-Asp-(Cx)-H wherein:
(Ch) is a chain of 1 to 20 amino acid residues containing at least 1 Arg residue or at least 3 Lys residues;
(Cx) is a chain of 1 to 20 amino acid residues selected from the group consisting of Ala, Arg, Asn, Asp, Glu, Gln, Gly, His, Ile, Leu, Met, Phe, Pro, Trp, Tyr, or Val; and each amino acid is in the (L) or (D) configuration.

37. A peptide according to claim 36 wherein (Ch) contains a total of four or more Lys residues or four or more Arg residues.

38. A peptide according to claim 37 wherein (Ch) contains at least one -Lys-Lys-, -Lys-Arg-, -Arg-Lys- or -Arg-Arg- linkage.

39. A peptide according to claim 37 wherein (Cx) is valine.

40. A peptide according to claim 36 selected from the group consisting of
H₂N-Arg-Arg-Arg-Arg-Arg-Arg-Arg-Arg-Arg-Gly-Asp-Val-H,
H₂N-Lys-Arg-Lys-Arg-Lys-Arg-Lys-Arg-Arg-Gly-Asp-Val-H,
H₂N-His-His-Arg-Arg-Arg-Arg-Arg-Arg-Arg-Gly-Asp-Val-H,
H₂N-His-His-Lys-Lys-Lys-Lys-Lys-Lys-Arg-Gly-Asp-Val-H,
H₂N-His-His-D-Ala-Arg-Lys-Arg-Lys-Gln-Arg-Gly-Asp-Val-H,
H₂N-His-His-D-Ala-Gly-Gly-Arg-Lys-Gln-Arg-Gly-Asp-Val-H,
H₂N-His-His-Lys-Arg-Lys-Arg-Lys-Gln-Arg-Gly-Asp-Val-H,
H₂N-Lys-Lys-Lys-Lys-Lys-Lys-Lys-Lys-Arg-Gly-Asp-Val-H,
H₂N-His-His-Leu-Arg-Lys-Arg-Lys-Gln-Arg-Gly-Asp-Val-H,
H₂N-His-His-Leu-Gly-Arg-Arg-Lys-Gln-Arg-Gly-Asp-Val-H,
H₂N-His-His-Leu-Arg-Gly-Arg-Lys-Gln-Arg-Gly-Asp-Val-H,
H₂N-His-His-Leu-Gly-Gly-Arg-Lys-Gln-Arg-Gly-Asp-Val-H, or
H₂N-His-His-Leu-Arg-Gly-Lys-Lys-Gln-Arg-Gly-Asp-Val.

41. A peptide according to claim 40 having the formula H₂N-Arg-Arg-Arg-Arg-Arg-Arg-Arg-Arg-Arg-Gly-Asp-Val-H.

42. A peptide according to claim 40 having the formula H₂N-Lys-Arg-Lys-Arg-Lys-Arg-Lys-Arg-Arg-Gly-Asp-Val-H.

43. A peptide according to claim 40 having the formula H₂N-His-His-Arg-Arg-Arg-Arg-Arg-Arg-Arg-Gly-Asp-Val-H.

44. A peptide according to claim 40 having the formula H₂N-His-His-Lys-Lys-Lys-Lys-Lys-Lys-Arg-Gly-Asp-Val-H.

45. A peptide according to claim 40 having the formula H₂N-His-His-D-Ala-Arg-Lys-Arg-Lys-Gln-Arg-Gly-Asp-Val-H.

46. A peptide according to claim 40 having the formula H₂N-His-His-D-Ala-Gly-Gly-Arg-Lys-Gln-Arg-Gly-Asp-Val-H.

47. A peptide according to claim 40 having the formula H₂N-His-His-Lys-Arg-Lys-Arg-Lys-Gln-Arg-Gly-Asp-Val-H.

48. A peptide according to claim 40 having the formula H₂N-Lys-Lys-Lys-Lys-Lys-Lys-Lys-Lys-Arg-Gly-Asp-Val-H.

49. A peptide according to claim 40 having the formula H₂N-His-His-Leu-Arg-Lys-Arg-Lys-Gln-Arg-Gly-Asp-Val-H.

50. A peptide according to claim 40 having the formula H₂N-His-His-Leu-Gly-Arg-Arg-Lys-Gln-Arg-Gly-Asp-Val-H.

51. A peptide according to claim 40 having the formula H₂N-His-His-Leu-Arg-Gly-Arg-Lys-Gln-Arg-Gly-Asp-Val-H.

52. A peptide according to claim 40 having the formula H₂N-His-His-Leu-Gly-Gly-Arg-Lys-Gln-Arg-Gly-Asp-Val-H.

53. A peptide according to claim 40 having the formula H₂N-His-His-Leu-Arg-Gly-Lys-Lys-Gln-Arg-Gly-Asp-Val-H.

54. A peptide having the formula H₂N-(Ch)-Arg-Gly-Asp-Val-H wherein (Ch) is a chain of amino acids selected from the group consisting of -His-His-Leu-Gly-Gly-Lys-Lys-Gln- or -His-His-Leu-Gly-Gly-Ala-Lys-Gln.

55. A peptide according to claim 54 having the formula H₂N-His-His-Leu-Gly-Gly-Lys-Lys-Gln-Arg-Gly-Asp-Val-H.

56. A peptide according to claim 54 having the formula H₂N-His-His-Leu-Gly-Gly-Ala-Lys-Gln-Arg-Gly-Asp-Val-H.

57. A peptide of the formula $H_2N-(X)_n-Arg-Gly-Asp-Val-H$ wherein:

$(X)_n$ is $-(Lys-Arg)_i-$ or $-(Lys)_i-$ and $i$ is an integer from 1–6; and each amino acid residue is in the (L) or (D) configuration.

58. A method for inhibiting the binding of fibrinogen to platelets comprising contacting the platelets with a peptide according to claim 34 in an amount of said peptide effective to inhibit said binding.

59. A method for inhibiting the binding of fibrinogen to platelets comprising contacting the platelets with a peptide according to claim 36 in an amount of said peptide effective to inhibit said binding.

60. A method for inhibiting the binding of fibrinogen to platelets comprising contacting the platelets with a peptide according to claim 40 in an amount of said peptide effective to inhibit said binding.

61. A method for inhibiting the binding of fibrinogen to platelets comprising contacting the platelets with a peptide according to claim 54 in an amount of said peptide effective to inhibit said binding.

62. A method for inhibiting the binding of fibrinogen to platelets comprising contacting the platelets with a peptide according to claim 57 in an amount of said peptide effective to inhibit said binding.

63. A method for inhibiting aggregation of cells to each other comprising contacting the cells with a peptide according to claim 34 in an amount of said peptide effective to inhibit said aggregation.

64. A method for inhibiting aggregation of cells to each other comprising contacting the cells with a peptide according to claim 36 in an amount of said peptide effective to inhibit said aggregation.

65. A method for inhibiting aggregation of cells to each other comprising contacting the cells with a peptide according to claim 40 in an amount of said peptide effective to inhibit said aggregation.

66. A method for inhibiting aggregation of cells to each other comprising contacting the cells with a peptide according to claim 54 in an amount of said peptide effective to inhibit said aggregation.

67. A method for inhibiting aggregation of cells to each other comprising contacting the cells with a peptide according to claim 57 in an amount of said peptide effective to inhibit said aggregation.

68. A method for inhibiting aggregation of platelets to each other comprising contacting the platelets with a peptide according to claim 34 in an amount of said peptide effective to inhibit said aggregation.

69. A method for inhibiting aggregation of platelets to each other comprising contacting the platelets with a peptide according to claim 36 in an amount of said peptide effective to inhibit said aggregation.

70. A method for inhibiting aggregation of platelets to each other comprising contacting the platelets with a peptide according to claim 40 in an amount of said peptide effective to inhibit said aggregation.

71. A method for inhibiting aggregation of platelets to each other comprising contacting the platelets with a peptide according to claim 54 in an amount of said peptide effective to inhibit said aggregation.

72. A method for inhibiting aggregation of platelets to each other comprising contacting the platelets with a peptide according to claim 57 in an amount of said peptide effective to inhibit said aggregation.

* * * * *